(12) United States Patent
Luzar

(10) Patent No.: US 9,474,698 B1
(45) Date of Patent: Oct. 25, 2016

(54) DENTAL HYGIENE ASSEMBLY

(71) Applicant: Brittany Luzar, Durango, CO (US)

(72) Inventor: Brittany Luzar, Durango, CO (US)

( * ) Notice: Subject to any disclaimer, the term of this patent is extended or adjusted under 35 U.S.C. 154(b) by 0 days.

(21) Appl. No.: 14/744,928

(22) Filed: Jun. 19, 2015

(51) Int. Cl.
| | | |
|---|---|---|
| *A61K 38/43* | (2006.01) |
| *A61K 8/02* | (2006.01) |
| *A23L 1/29* | (2006.01) |
| *A23L 1/302* | (2006.01) |
| *A23L 1/30* | (2006.01) |
| *A21D 13/08* | (2006.01) |
| *A61Q 11/00* | (2006.01) |
| *A61K 8/34* | (2006.01) |
| *A61K 8/73* | (2006.01) |
| *A61K 8/19* | (2006.01) |
| *A61K 8/25* | (2006.01) |
| *A61K 8/365* | (2006.01) |

(52) U.S. Cl.
CPC ............. *A61K 8/0216* (2013.01); *A21D 13/08* (2013.01); *A23L 1/293* (2013.01); *A23L 1/302* (2013.01); *A23L 1/3002* (2013.01); *A61K 8/19* (2013.01); *A61K 8/25* (2013.01); *A61K 8/345* (2013.01); *A61K 8/365* (2013.01); *A61K 8/73* (2013.01); *A61Q 11/00* (2013.01); *A23V 2002/00* (2013.01); *A61K 2800/30* (2013.01); *A61K 2800/5922* (2013.01); *A61K 2800/92* (2013.01)

(58) Field of Classification Search
CPC ....................................................... A61K 8/345
USPC ........................................................... 424/49
See application file for complete search history.

(56) References Cited

U.S. PATENT DOCUMENTS

| | | | |
|---|---|---|---|
| 7,500,576 B1 | 3/2009 | Alvarez | |
| 8,214,962 B2 | 7/2012 | Rohrig | |
| 8,678,823 B2 | 3/2014 | Wagner et al. | |
| 2005/0158252 A1* | 7/2005 | Romanowski | A61K 8/345 |
| | | | 424/49 |
| 2007/0154409 A1 | 7/2007 | Annis | |
| 2007/0208380 A1 | 9/2007 | Ebner | |
| 2010/0034871 A1 | 2/2010 | Mikkelsen et al. | |

* cited by examiner

*Primary Examiner* — Jake Vu

(57) ABSTRACT

A dental hygiene assembly includes a biscuit that may be eaten by a user. The biscuit is comprised of a mixture that may clean teeth of the user. The mixture comprises rice flour, white whole wheat flour, wheat starch, sugar, whole grain oat flour, flavor powder, tricalcium phosphate, dicalcium phosphate, natural flavor, mixed tocopherols, zinc sulfate, vitamin E powder, electrolytic iron, annatto extract and fluoride free toothpaste.

7 Claims, 4 Drawing Sheets

DENTAL HYGIENE ASSEMBLY

BACKGROUND OF THE DISCLOSURE

Field of the Disclosure

The disclosure relates to hygiene devices and more particularly pertains to a new hygiene device for cleaning a user's teeth while the user learns to brush the user's teeth.

SUMMARY OF THE DISCLOSURE

An embodiment of the disclosure meets the needs presented above by generally comprising a biscuit that may be eaten by a user. The biscuit is comprised of a mixture that may clean teeth of the user. The mixture comprises rice flour, white whole wheat flour, wheat starch, sugar, whole grain oat flour, flavor powder, tricalcium phosphate, dicalcium phosphate, natural flavor, mixed tocopherols, zinc sulfate, vitamin E powder, electrolytic iron, annatto extract and fluoride free toothpaste.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
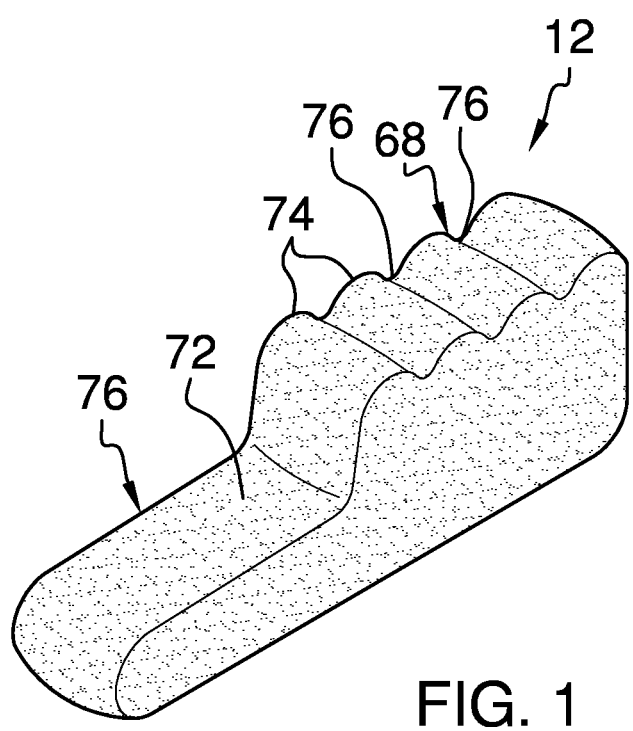
FIG. 1 is a perspective view of a dental hygiene assembly according to an embodiment of the disclosure.
Figure 2:
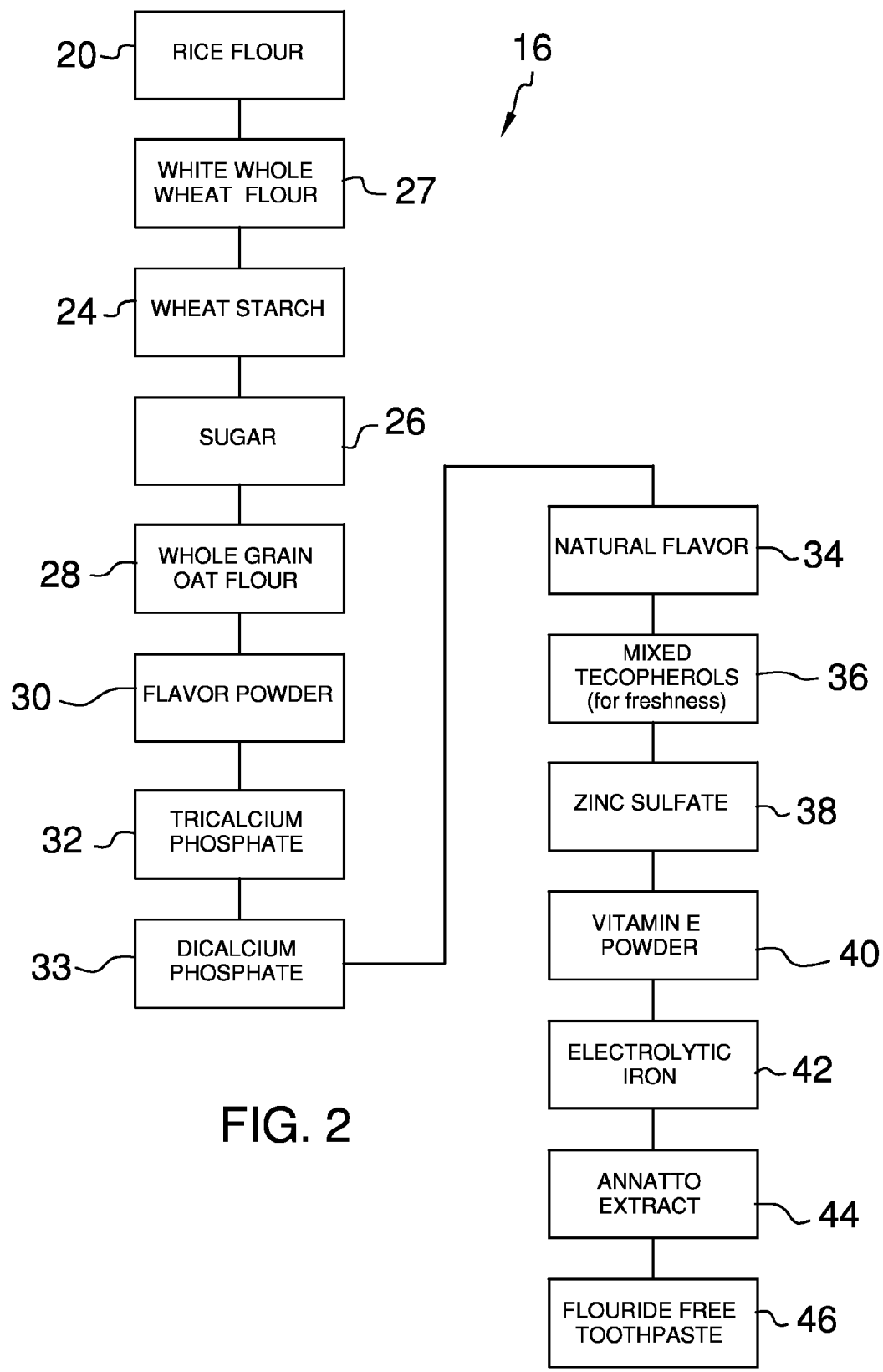
FIG. 2 is a schematic view of an embodiment of the disclosure.
Figure 3:
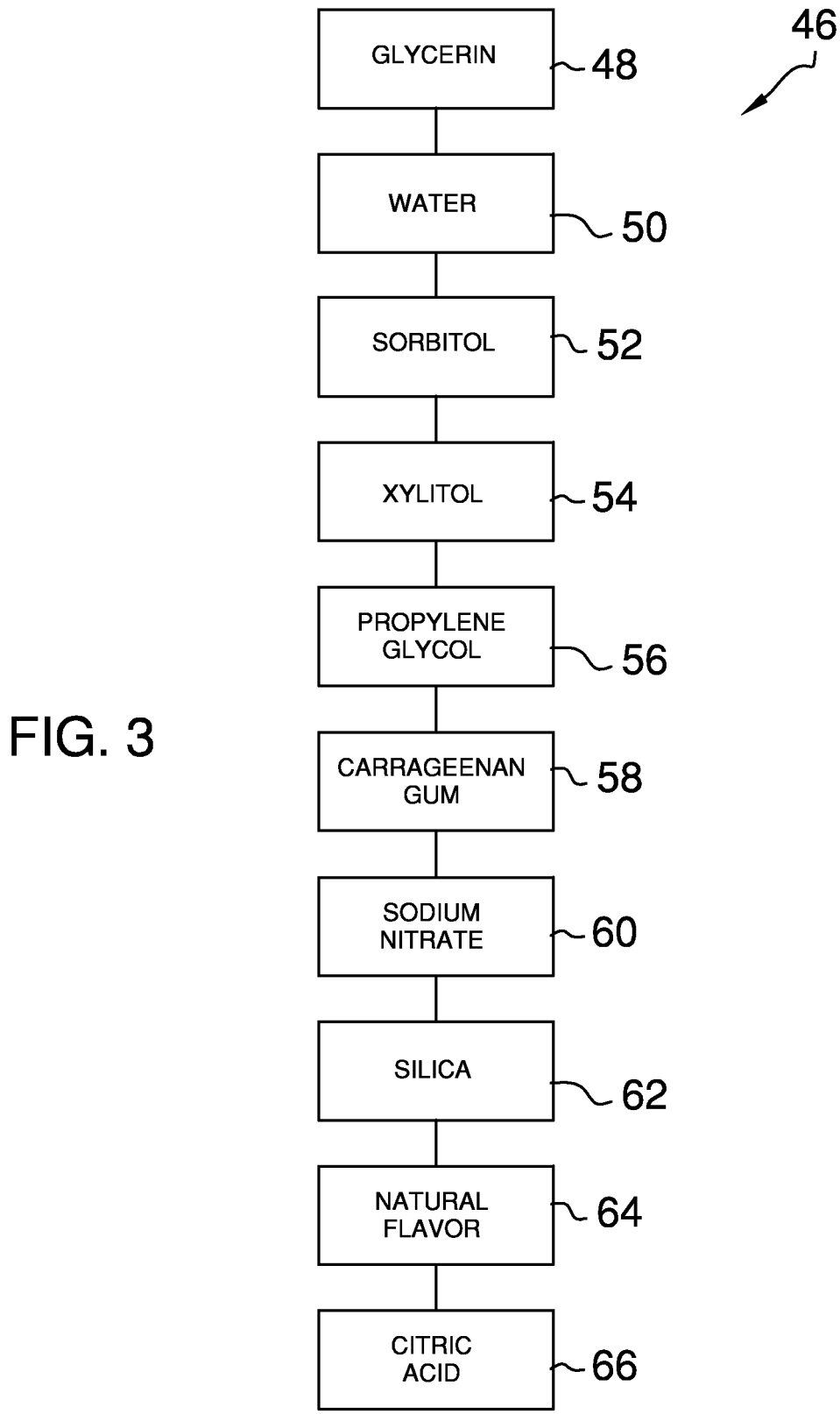
FIG. 3 is a schematic view of an embodiment of the disclosure.
Figure 4:
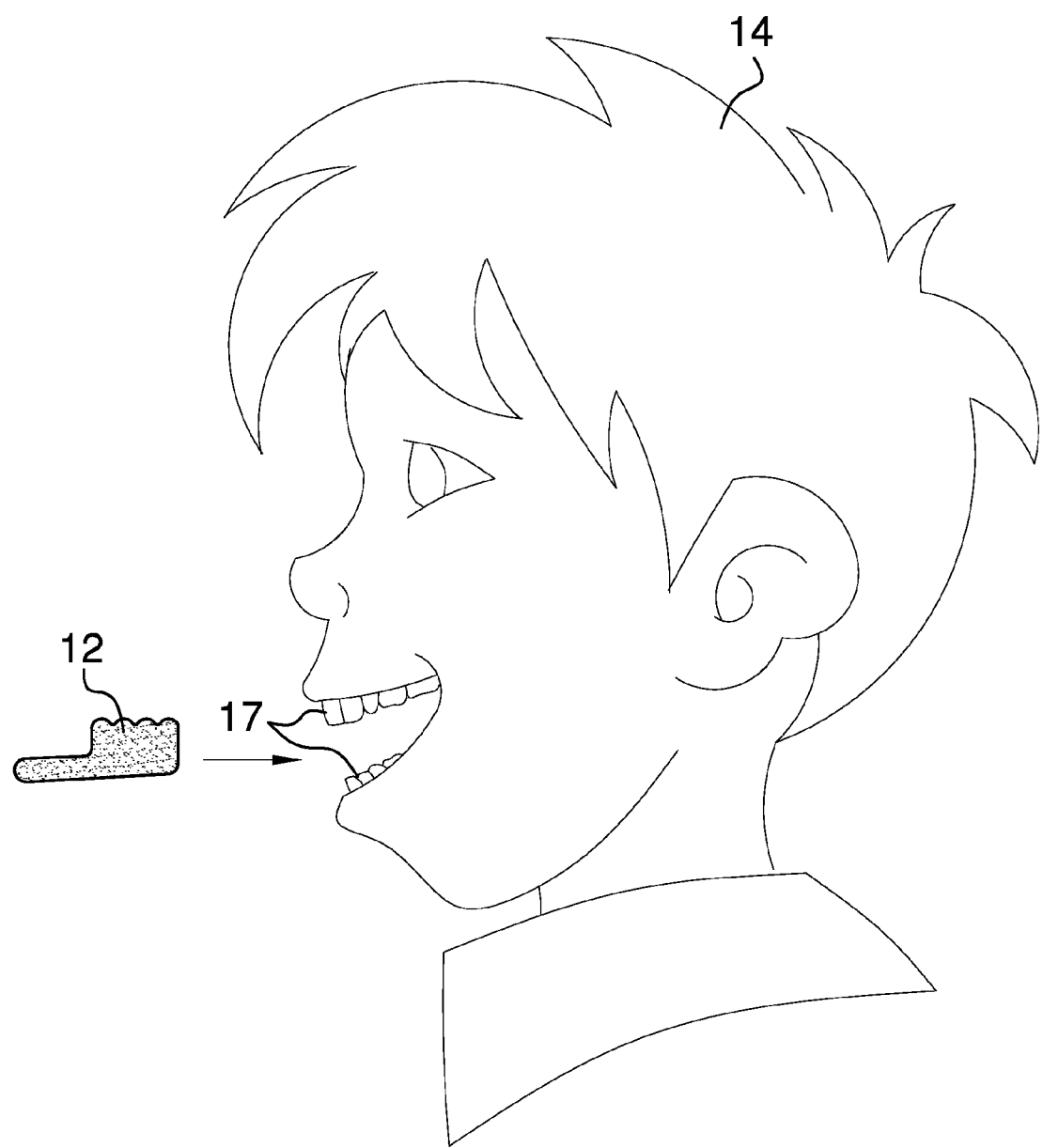
FIG. 4 is a perspective in-use view of an embodiment of the disclosure.

With reference now to the drawings, and in particular to FIGS. 1 through 4 thereof, a new hygiene device embodying the principles and concepts of an embodiment of the disclosure and generally designated by the reference numeral 10 will be described.

As best illustrated in FIGS. 1 through 4, the dental hygiene assembly 10 generally comprises a biscuit 12 that may be eaten by a user 14. The biscuit 12 is comprised of a mixture 16 to clean the user's teeth 17. The user 14 may be a toddler that has not yet learned to brush their teeth 17.

The mixture 18 comprises approximately equal parts of rice flour 20, white whole wheat flour 22, wheat starch 24, sugar 26, whole grain oat flour 28, and flavor powder 30. Each of the rice flour 20, the white whole wheat flour 22, the white starch 24, the sugar 26, the whole grain out flour 28 and the flavor powder 30 comprise greater than 2% of the total mixture 16. The mixture further comprises tricalcium phosphate 32, dicalcium phosphate 33, natural flavor 34, mixed tocopherols 36, zinc sulfate 38, vitamin E powder 40, electrolytic iron 42, annatto extract 44 and fluoride free toothpaste 46. The mixed tocopherols 36 help to maintain a freshness of the biscuit 12.

Each of the tricalcium phosphate 32, the dicalcium phosphate 33, the natural flavor 34, the mixed tocopherols 36, the zinc sulfate 38, the vitamin E powder 40, the electrolytic iron and the annatto extract 44 comprise less than 2% of the total mixture 16. The fluoride free toothpaste 46 comprises glycerin 48, water 50, sorbitol 52, xylitol 54, propylene glycol 56, carrageenan gum 58, sodium nitrate 60, silica 62, natural flavor 64, and citric acid 66. The natural flavor 64 of the mixture 18 may have, but not be limited to, an apple-banana flavor, a blueberry flavor, a cheery flavor or a pineapple-mange flavor The biscuit 12 has first portion 68, a second portion 70 and a top edge 72. The top edge 72 corresponding to the first portion 68 has an alternating sequence of hills 74 and depressions 76. The hills 74 and depressions 76 are distributed along the first portion 68. The first portion 68 has a height that is greater than a height of the second portion 70 such that the biscuit 12 is toothbrush shaped.

In use, the biscuit 12 is eaten by the user 14 while the user 14 is learning to brush the user's teeth. The biscuit promotes proper dental hygiene while the user is learning to brush the user's teeth. The biscuit allows the user's teeth to be cleaned without the need to have fingers inserted into the user's mouth thereby preventing the fingers from being bitten.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A dental hygiene assembly configured to be chewed by a user thereby cleaning the user's teeth, said assembly comprising:
   a biscuit configured to be eaten by a user, said biscuit being comprised of a mixture configured to clean teeth of the user, said mixture comprising:
   rice flour,
   white whole wheat flour,
   wheat starch,
   sugar,
   whole grain oat flour,
   flavor powder, tricalcium phosphate,
dicalcium phosphate,
natural flavor,
mixed tocopherols,
zinc sulfate,
vitamin E powder,
electrolytic iron,
annatto extract, and
fluoride free toothpaste.

2. The assembly according to claim 1, wherein:
said rice flour comprises greater than approximately 2% of said mixture,
said white whole wheat flour comprises greater than approximately 2% of said mixture,
said wheat starch comprises greater than approximately 2% of said mixture,
said sugar comprises greater than approximately 2% of said mixture,
said whole grain oat flour comprises greater than approximately 2% of said mixture, and
said flavor powder comprises greater than approximately 2% of said mixture.

3. The assembly according to claim 1, wherein:
said dicalcium phosphate comprises less than approximately 2% of said mixture,
said tricalcium phosphate comprises less than approximately 2% of said mixture,
natural flavor comprises less than approximately 2% of said mixture, mixed tocopherols comprises less than approximately 2% of said mixture, zinc sulfate comprises less than approximately 2% of said mixture, vitamin E powder, said vitamin E powder comprises less than approximately 2% of said mixture,
electrolytic iron comprises less than approximately 2% of said mixture, and
annatto extract comprises less than approximately 2% of said mixture.

4. The assembly according to claim 1, wherein said fluoride free toothpaste comprises:
glycerin,
water,
sorbitol,
xylitol,
propylene glycol,
carrageenan gum,
sodium nitrate,
silica,
natural flavor, and
citric acid.

5. The assembly according to claim 1, wherein said biscuit has first portion, a second portion and a top edge, said top edge corresponding to said first portion having an alternating sequence of hills and depressions.

6. The assembly according to claim 4, wherein said hills and depressions are distributed along said first portion, said first portion having a height being greater than a height of said second portion wherein said biscuit is toothbrush shaped.

7. A dental hygiene assembly configured to be chewed by a user thereby cleaning the user's teeth, said assembly comprising:
a biscuit configured to be eaten by a user, said biscuit being comprised of a mixture configured to clean teeth of the user, said mixture comprising:
rice flour comprising greater than approximately 2% of said mixture, white whole wheat flour comprising greater than approximately 2% of said mixture,
wheat starch comprising greater than approximately 2% of said mixture, sugar comprising greater than approximately 2% of said mixture, whole grain oat flour comprising greater than approximately 2% of said mixture,
flavor powder comprising greater than approximately 2% of said mixture, tricalcium phosphate comprising less than approximately 2% of said mixture,
dicalcium phosphate comprising less than approximately 2% of said mixture,
natural flavor comprising less than approximately 2% of said mixture, mixed tocopherols comprising less than approximately 2% of said mixture,
zinc sulfate comprising less than approximately 2% of said mixture, vitamin E powder, said vitamin E powder comprising less than approximately 2% of said mixture,
electrolytic iron comprising less than approximately 2% of said mixture, annatto extract comprising less than approximately 2% of said mixture, and
fluoride free toothpaste, said fluoride free toothpaste comprising:
glycerin,
water,
sorbitol,
xylitol,
propylene glycol,
carrageenan gum,
sodium nitrate,
silica,
natural flavor, and
citric acid; and
said biscuit having first portion, a second portion and a top edge, said top edge corresponding to said first portion having an alternating sequence of hills and depressions, said hills and depressions being distributed along said first portion, said first portion having a height being greater than a height of said second portion wherein said biscuit is toothbrush shaped.

* * * * *